United States Patent
Gu

(10) Patent No.: US 12,328,649 B2
(45) Date of Patent: Jun. 10, 2025

(54) OPTIMIZATION OF EDGE COMPUTING DISTRIBUTED NEURAL PROCESSOR FOR WEARABLE DEVICES

(71) Applicant: Northwestern University, Evanston, IL (US)

(72) Inventor: Jie Gu, Evanston, IL (US)

(73) Assignee: Northwestern University, Evanston, IL (US)

( * ) Notice: Subject to any disclaimer, the term of this patent is extended or adjusted under 35 U.S.C. 154(b) by 1039 days.

(21) Appl. No.: 17/286,330

(22) PCT Filed: Oct. 21, 2019

(86) PCT No.: PCT/US2019/057255
§ 371 (c)(1),
(2) Date: Apr. 16, 2021

(87) PCT Pub. No.: WO2020/082080
PCT Pub. Date: Apr. 23, 2020

(65) Prior Publication Data
US 2021/0383201 A1 Dec. 9, 2021

Related U.S. Application Data

(60) Provisional application No. 62/748,075, filed on Oct. 19, 2018.

(51) Int. Cl.
*A61F 2/72* (2006.01)
*A61B 5/00* (2006.01)
(Continued)

(52) U.S. Cl.
CPC .............. *H04W 4/38* (2018.02); *A61B 5/486* (2013.01); *A61F 2/72* (2013.01); *G06F 18/214* (2023.01);
(Continued)

(58) Field of Classification Search
CPC .......... G06N 3/047; G06N 3/063; G06N 3/08; G06F 18/214; G06F 18/251; A61F 2/72; H04W 4/38; G11C 11/54; A61B 5/486
See application file for complete search history.

(56) References Cited

U.S. PATENT DOCUMENTS

| | | | |
|---|---|---|---|
| 7,048,697 B1 * | 5/2006 | Mitsuru | ............... A61B 5/6892 600/595 |
| 2003/0236760 A1 | 12/2003 | Nugent | |

(Continued)

OTHER PUBLICATIONS

Hwanjo Yu, Jinoh Oh, and Wook-Shin Han. 2009. Efficient feature weighting methods for ranking. In Proceedings of the 18th ACM conference on Information and knowledge management (CIKM '09). Association for Computing Machinery, New York, NY, USA, 1157-1166. (Year: 2009).*

(Continued)

*Primary Examiner* — Kamran Afshar
*Assistant Examiner* — Brian J Hales
(74) *Attorney, Agent, or Firm* — Benesch Friedlander Coplan & Aronoff LLP

(57) ABSTRACT

Systems and/or methods may include an edge-computing distributed neural processor to effectively reduce the data traffic and physical wiring congestion. A local and global networking architecture may reduce traffic among multi-chips in edge computing. A mixed-signal feature extraction approach with assistance of neural network distortion recovery is also described to reduce the silicon area. High precision in signal features classification with a low bit processing circuitry may be achieved by compensating with a recursive stochastic rounding routine, and provide on-chip learning to re-classify the sensor signals.

19 Claims, 11 Drawing Sheets

(51) Int. Cl.
*G06F 18/214* (2023.01)
*G06F 18/25* (2023.01)
*G06N 3/047* (2023.01)
*G06N 3/063* (2023.01)
*G06N 3/08* (2023.01)
*G11C 11/54* (2006.01)
*H04W 4/38* (2018.01)

(52) U.S. Cl.
CPC ........... *G06F 18/251* (2023.01); *G06N 3/047* (2023.01); *G06N 3/063* (2013.01); *G06N 3/08* (2013.01); *G11C 11/54* (2013.01)

(56) References Cited

U.S. PATENT DOCUMENTS

| | | | |
|---|---|---|---|
| 2011/0300851 | A1 | 12/2011 | Krishnaswamy et al. |
| 2014/0031952 | A1* | 1/2014 | Harshbarger ........ A61B 5/7264 623/25 |
| 2017/0220923 | A1* | 8/2017 | Bae .......................... G06N 3/08 |
| 2018/0330238 | A1* | 11/2018 | Luciw ..................... G06N 3/045 |
| 2019/0197549 | A1* | 6/2019 | Sharma .................... G06N 3/08 |

OTHER PUBLICATIONS

M. Seiffert, F. Holstein, R. Schlosser and J. Schiller, "Next Generation Cooperative Wearables: Generalized Activity Assessment Computed Fully Distributed Within a Wireless Body Area Network," in IEEE Access, vol. 5, pp. 16793-16807, 2017 (Year: 2017).*

M. Magno, M. Pritz, P. Mayer and L. Benini, "DeepEmote: Towards multi-layer neural networks in a low power wearable multi-sensors bracelet," 2017 7th IEEE International Workshop on Advances in Sensors and Interfaces (IWASI), Vieste, Italy, 2017, pp. 32-37 (Year: 2017).*

Dubey et al., "Fog computing in medical internet-of-things: architecture, implementation, and applications.", In: Handbook of Large-Scale Distributed Computing in Smart Healthcare dated Jun. 24, 2017, Retrieved on Dec. 13, 2019 from <https://arxiv.org/pdf/1706.08012.pdf>, 29 pages.

Yu et al., "Efficient feature weighting methods for ranking.", In: Proceedings of the 18th ACM conference on Information and knowledge management dated Nov. 6, 2009, Retrieved on Dec. 13, 2019 from <http://citeseerx.ist.psu.edu/viewdoc/download?doi=10.1.1.613.3780&rep=rep1&type=pdf>, 9 pages.

International Search Report and Written Opinion dated Jan. 9, 2020 for PCT Application No. PCT/US2019/057255, 9 pages.

D. Farina, et al., "The extraction of neural information from the surface EMG for the control of upper-limb prostheses: emerging avenues and challenges," IEEE Transactions on Neural Systems and Rehabilitation Engineering, vol. 22, No. 4, pp. 797-809, 2014.

N. Helleputte, et al., "A 345 µW multi-sensor biomedical SoC with bioimpedance, 3-channel ECG, motion artifact reduction, and integrated Dsp", IEEE Journal of Solid-State Circuits, vol. 50, No. 1, pp. 230-244, Jan. 2015.

A. Young, et al., "Analysis of using EMG and mechanical sensors to enhance intent recognition in powered lower limb prostheses," Journal of Neural Engineering, vol. 11, No. 5, Sep. 2014.

S. Wurth, et al., "A real-time comparison between direct control, sequential pattern recognition control and simultaneous pattern recognition control using a fitts' law style assessment procedure", Journal of NeuroEngineering and Rehabilitation, vol. 11, No. 1, 2014.

A. Adewuyi, et al., "An analysis of intrinsic and extrinsic hand muscle EMG for improved pattern recognition control", IEEE Transactions on Neural Systems and Rehabilitation Engineering, vol. 24, No. 4, pp. 485-494, 2016.

N. Krausz, et al., "Depth sensing for improved control of lower limb prostheses", IEEE Transactions on Biomedical Engineering, vol. 62, No. 11, pp. 2576-2587, 2015.

M. Atzori, et al., "Electromyography data for non-invasive naturally-controlled robotic hand prostheses," in Scientific Data, 1:140053, Dec. 2014.

N. Krausz, L. Hargrove, "Recognition of ascending stairs from 2D images for control of powered lower limb prostheses", IEEE Inter. Conf. in Medicine and Biology Society (EMBC), 2015.

A. Jamthe, et al., "Harnessing big data for wireless body area network applications", International Conf. on Computational Intelligence and Communication Networks (INFOCOM), 2015.

G. Almashaqbeh, et al., "A cloud-based interference-aware remote health monitoring system for non-hospitalized patients", Symposium on Selected Areas in Communications, 2014.

H. Dubey, et al., "Fog Computing in Medical Internet-of-Things: Architecture, Implementation, and Applications", arXiv: 1706.08012, 2017.

W. Shi, et al., "Edge computing: vision and challenges", IEEE Internet of Things Journal, vol. 3, No. 5, pp. 637-646, Oct. 2016.

M. Satyanarayanan, "The emergence of edge computing", Computer, vol. 50, No. 1, pp. 30-39, Jan. 2017.

B. Calhoun, et al., "Body sensor networks: a holistic approach from silicon to users", Proceedings of the IEEE, vol. 100, No. 1, pp. 91-106, Jan. 2012.

K. AL-Tamimi, et al., "Preweighted Linearized VCO Analog-to Digital Converter," in IEEE Transactions on Very Large Scale Integration (VLSI) Systems, vol. 435, pp. 1983-1987, Jun. 2017.

N. Desai, et al., "A scalable, 2.9 mW, 1 Mb/s e-textiles body area network transceiver with remotely-powered nodes and bi-directional data communication", IEEE Journal of Solid-State Circuits, vol. 49, No. 9, pp. 1995-2004, Sep. 2014.

J. Yoo, et al., "An 8-channel scalable EEG acquisition SoC with fully integrated patient-specific seizure classification and recording processor," ISSCC, pp. 292-294, Feb. 2014.

S. Yin, et al., "A 1.06 µW smart ECG processor in 65 nm CMOS for realtime biometric authentication and personal cardiac monitoring," Symposium on VLSI Circuits, Jun. 2017.

S. Benatti, et al., "A sub-10mW real-time implementation for EMG hand gesture recognition based on a multi-core biomedical SoC," IWASI, pp. 139-144, Jul. 2017.

\* cited by examiner

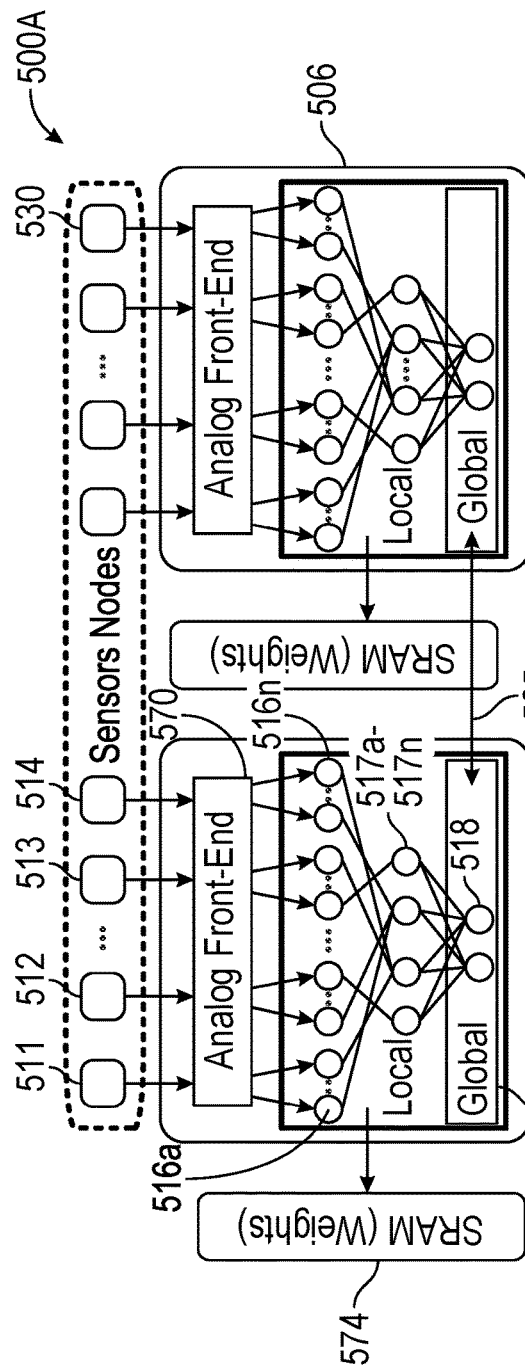
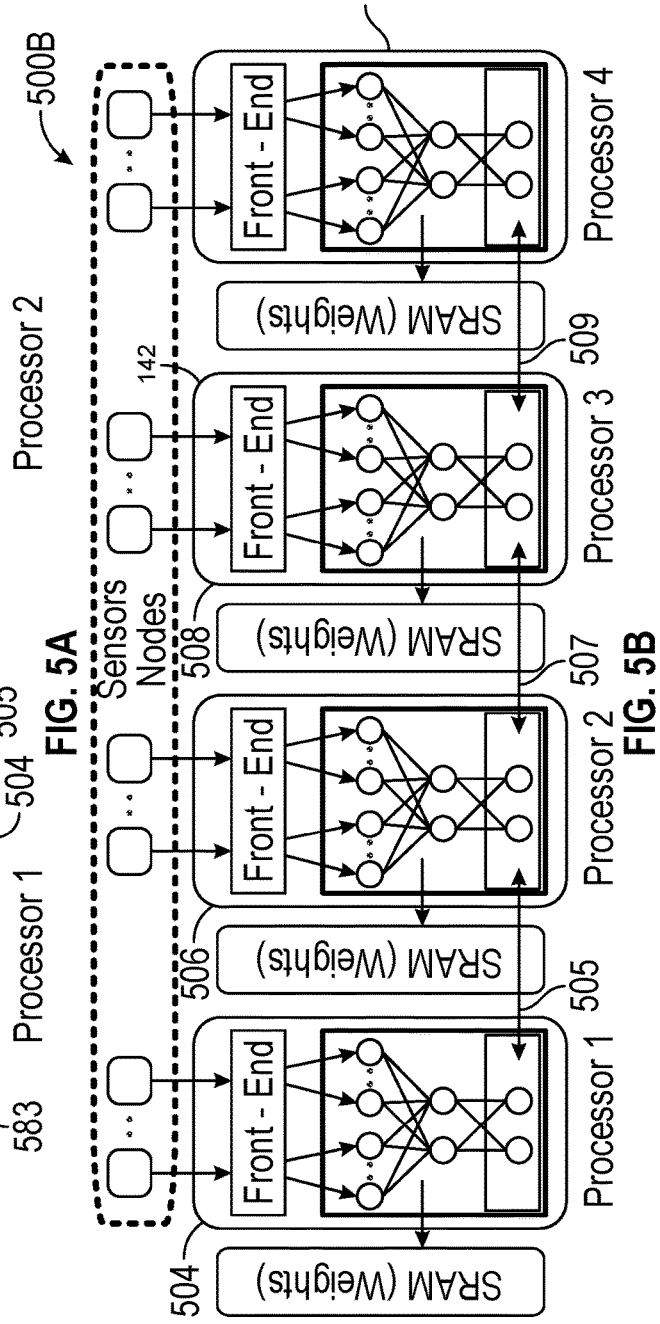
FIG. 5A
FIG. 5B

OPTIMIZATION OF EDGE COMPUTING DISTRIBUTED NEURAL PROCESSOR FOR WEARABLE DEVICES

CROSS-REFERENCE TO RELATED APPLICATION

This application is a National Stage of PCT/US2019/057255 titled "Design and Optimization of Edge Computing Distributed Neural Processor for Wearable Devices," filed on Oct. 21, 2019, which claims priority and the benefit of U.S. Provisional Patent Application Ser. No. 62/748,075 titled "Design and Optimization of Edge Computing Distributed Neural Processor for Wearable Devices," filed on Oct. 19, 2018. The entire contents of the above-identified applications are incorporated herein by reference.

STATEMENT OF FEDERALLY FUNDED RESEARCH OR SPONSORSHIP

The inventions were made with government support under the National Science Foundation grant CNS1816870. The government has certain rights in the inventions.

BACKGROUND

Some modern biomedical devices such as prosthetic devices use sensor fusion techniques to improve the classification accuracy of an intended motion in rehabilitation applications. Motion classifier are difficult to design due to the large number of channels they use and the stringent communication latency requirements they must achieve.

BRIEF DESCRIPTION OF DRAWINGS

FIGS. 5A and 5B are exemplary optimizations used in a distributed neural network.

DETAILED DESCRIPTION

Edge computing neural processing (NP) systems may be integrated into energy efficient wearable devices, Internet of Things (IoT) devices, biomedical signal processing, etc. In some applications, the systems achieve ultra-low power consumption, are easy to implement and/or achieve low latency/computing times. Some systems may process physiological signals, such as electromyography (EMG) or electrocardiography (ECG), in wearable devices. Such devices may be used in broad application spaces including artificial intelligence (AI), virtual reality, gaming, biomedical rehabilitation, etc. Currently, to process physiological signals, technology relies on high-end embedded microprocessors or personal computers to execute desired functions. State-of-art edge processing devices or wearable devices do not have built-in machine learning functions that process physiological signals such as EMG and ECG signals. Without this processing capability, large amounts of sensor data usually must be transferred to a centralized microprocessor resulting in large communication overheads and heavy processing loads. In the disclosed systems, an integrated circuit includes a built-in machine learning capability, a distributed networking capability and a special body channel communication. The systems are efficient and consume less than ten thousand times the amount of power some microprocessors consume. The system's bandwidth efficiency also minimizes communication bottlenecks that typically occur.

Figure 7A:
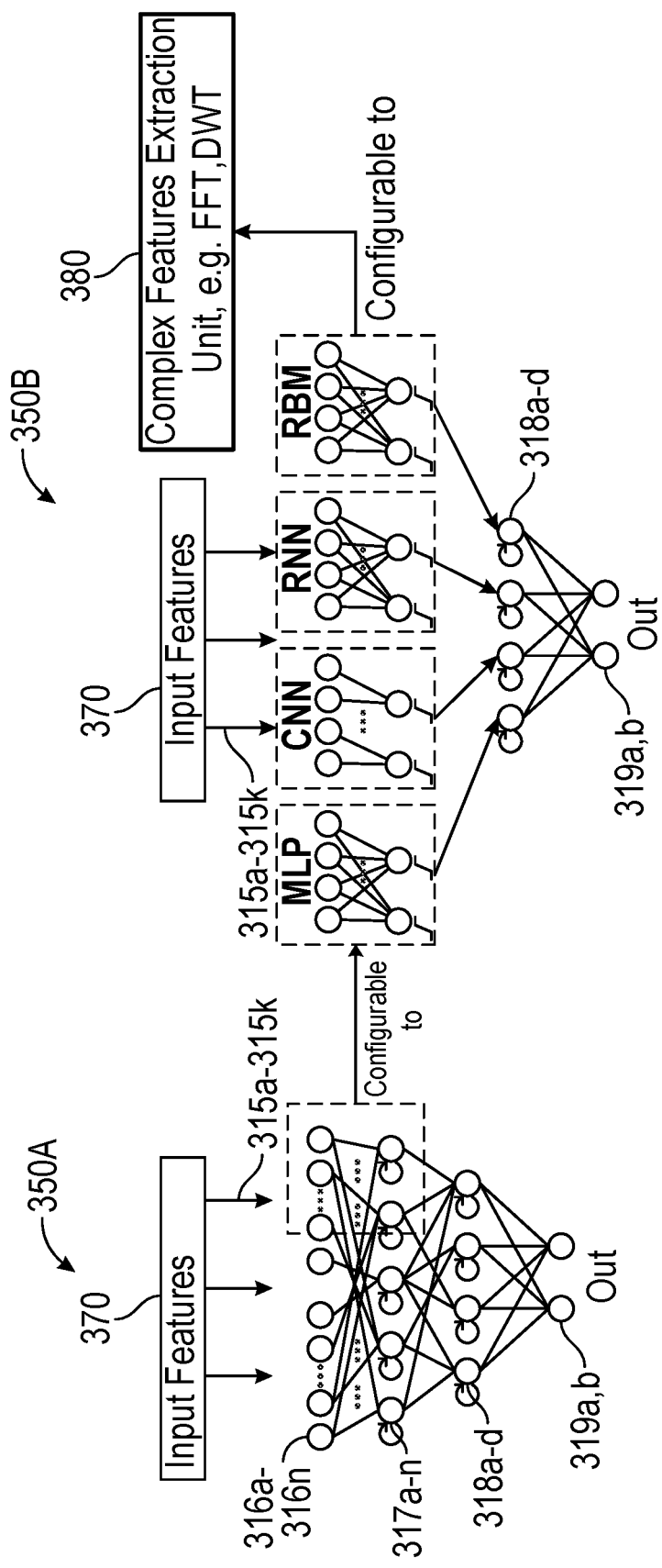
FIGS. 7A and 7B are an exemplary neural processor reconfigured to implement an on-chip machine.
Figure 7B:
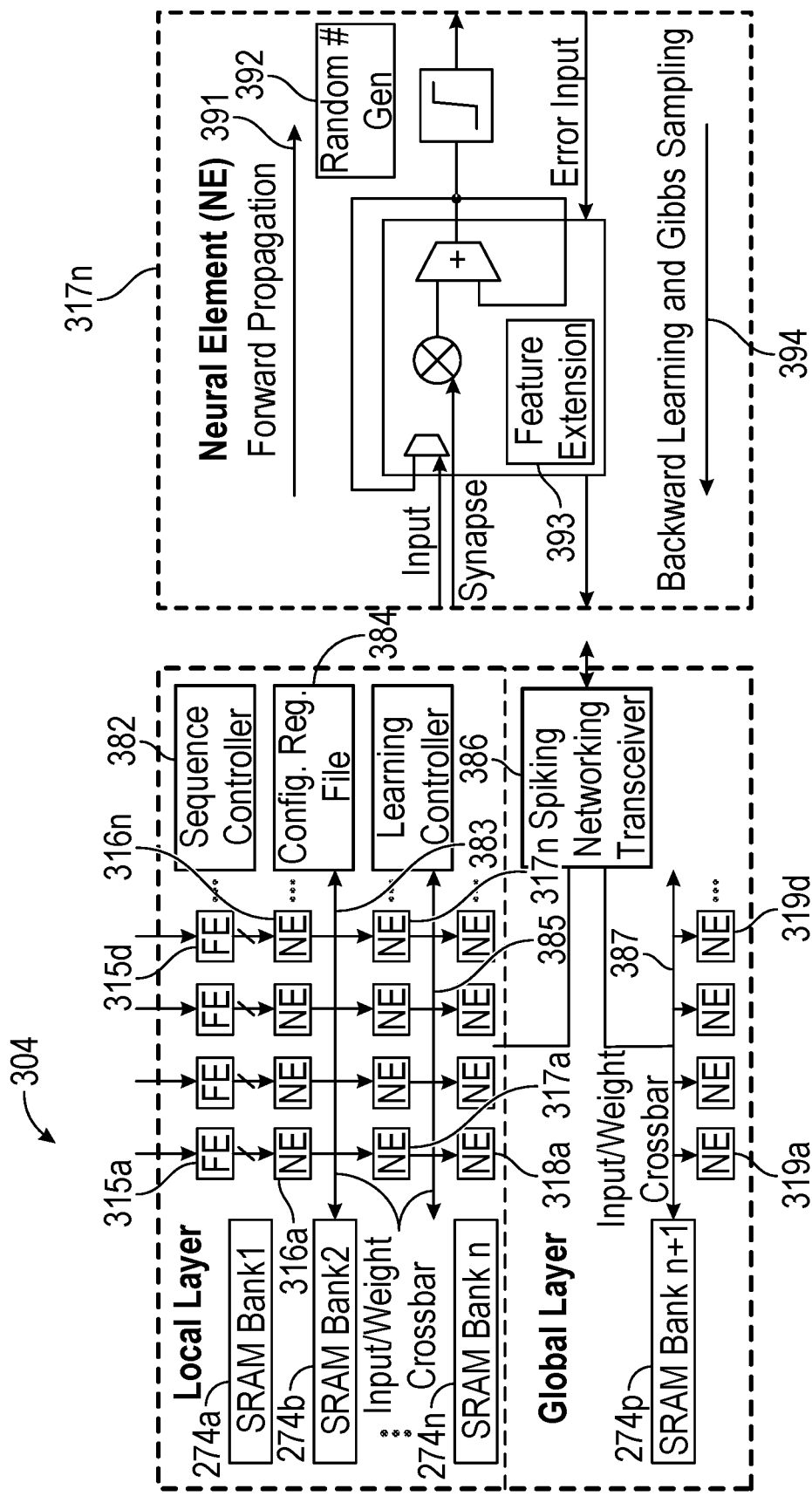
Figure 8A:
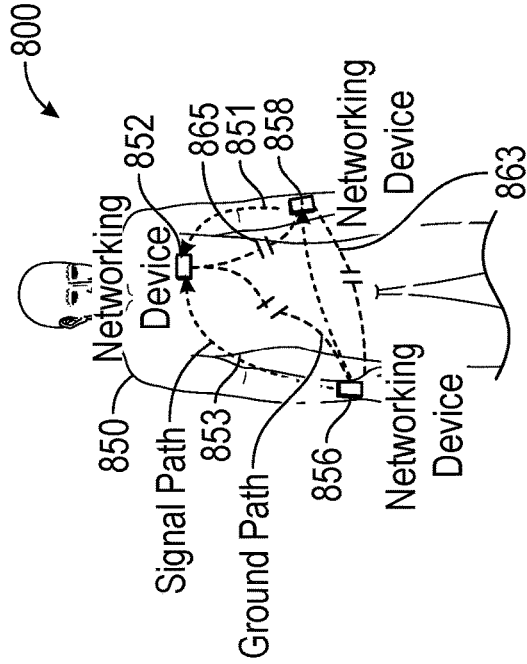
FIGS. 8A and 8B are an exemplary capacitive body channel that facilitates communication among neural processors in a distributed neural network.
Figure 8B:
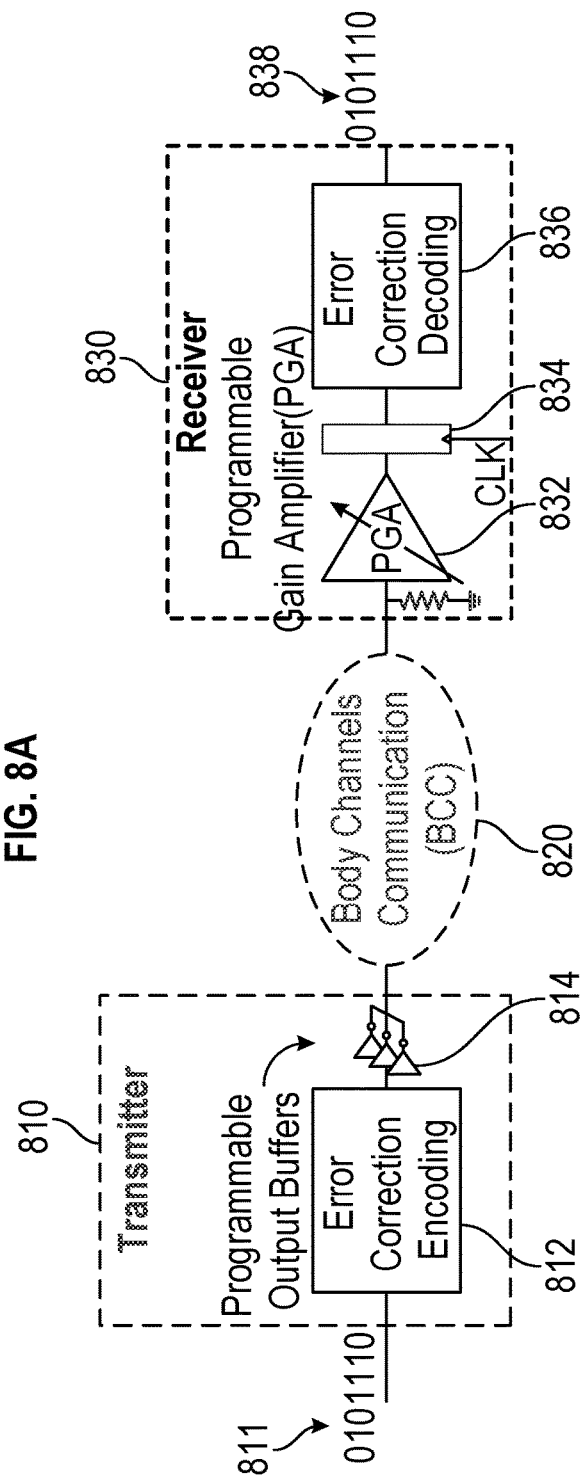
Figure 9:
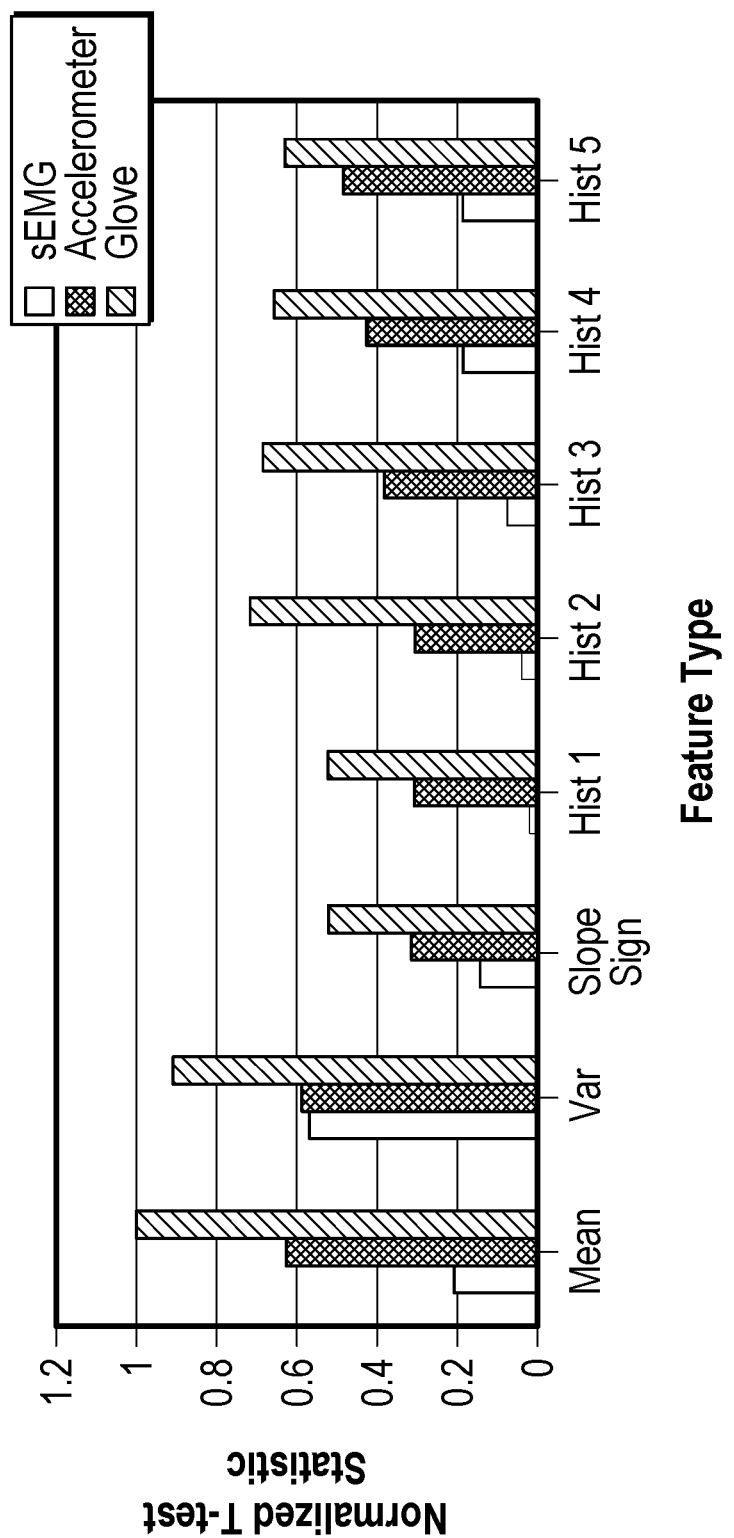
FIG. 9 is a feature rank score chart of an individual heterogeneous sensor optimized for fusing or combining features.

Some systems are also used in human cognitive assistance, virtual reality, neural network accelerators, physiological signal processing, wearable devices, etc. The machine learning operation (see FIGS. 7A, 7B and 9) are distributed across multiple units in some systems that are connected through a distributed neural network. Such systems can result in about an eighty-times reduction in communication traffic. A mixed-signal feature extraction (see FIGS. 6A-6D), e.g., replacing some or all analog-to-digital converters (ADC), may achieve about a twenty-eight-times reduction in chip surface area. In some applications, a body channel communication (BCC) as shown in FIGS. 8A and 8B replaces conventional wireless communication technology, e.g., WIFI or Bluetooth. These systems may consume about ten to one-hundred times less power than conventional systems and suffer from less wireless interference. In some applications, an Application Specific Integrated Circuit (ASIC) chip with a built-in machine learning capability as shown in FIGS. 7A, 7B, and 9 provides physiological signal analysis for human assistance.

Figure 1A:
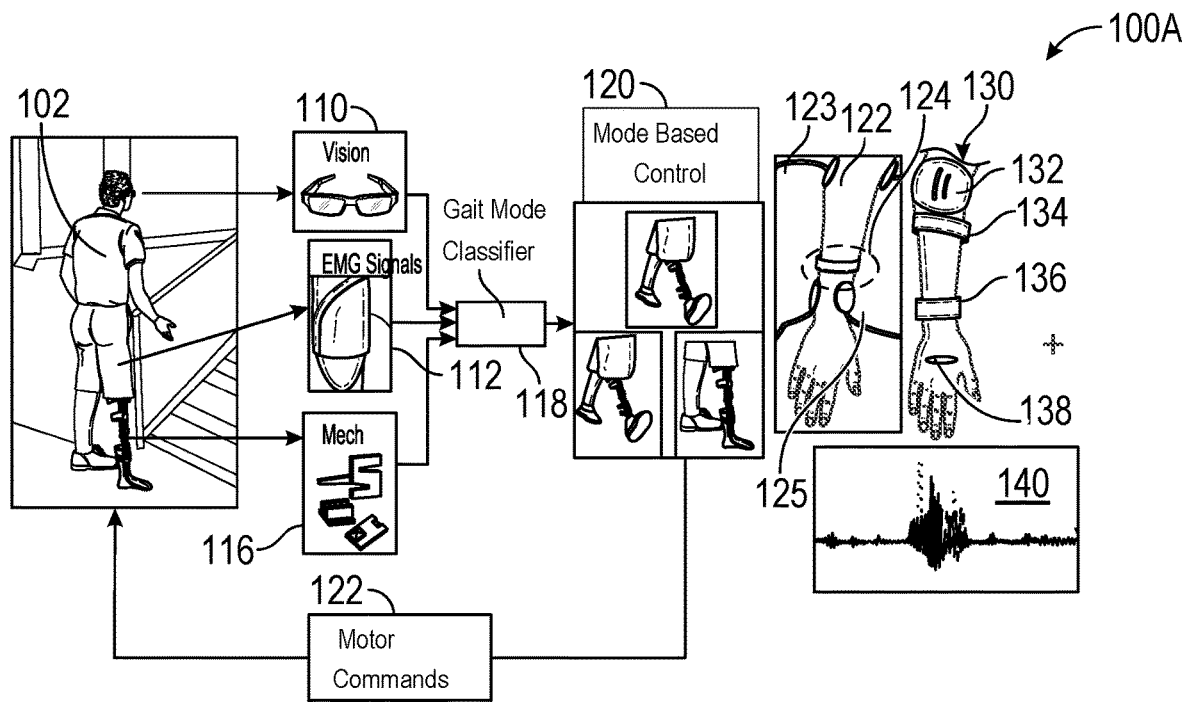
FIGS. 1A and 1B are exemplary implementations of edge computing distributed neural processors that are part of wearable devices.
Figure 1B:
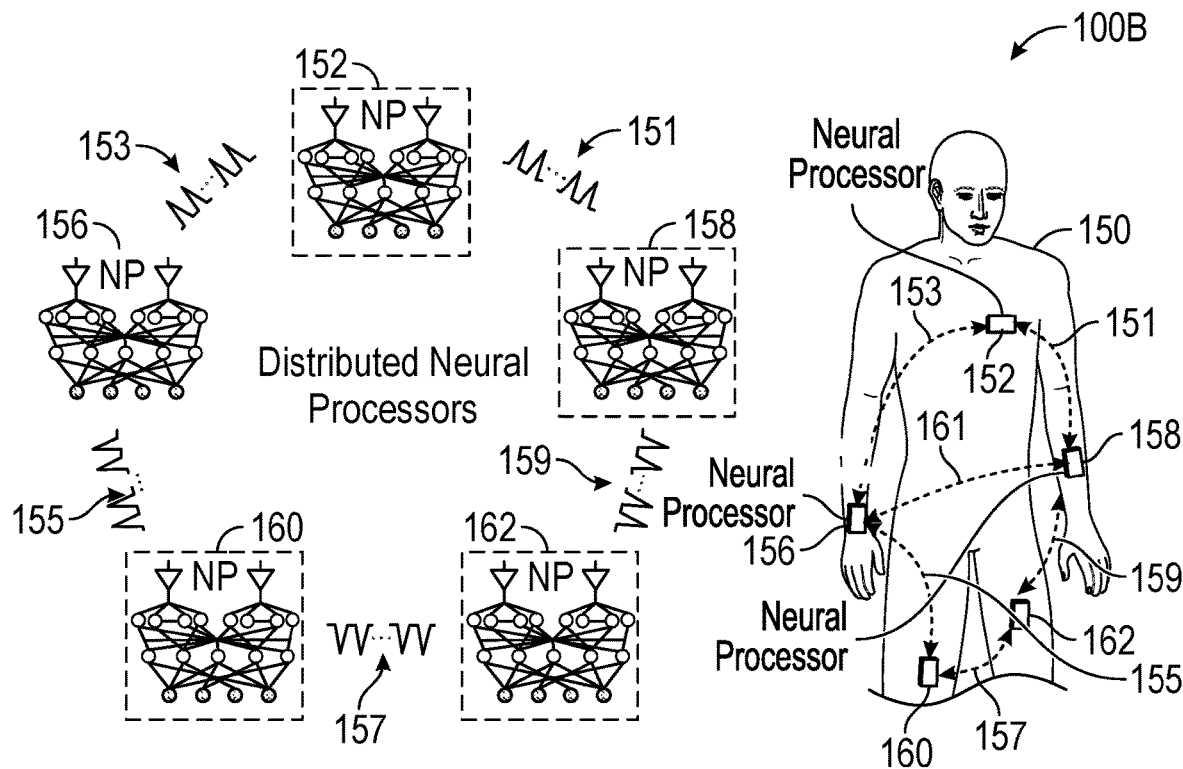

Systems such as those shown in FIGS. 1A and 1B may include an edge-computing distributed neural processor to effectively reduce the data traffic congestion and physical wiring. A local and global networking architecture shown in FIGS. 2-4 may significantly reduce traffic among multichips in edge computing. A mixed-signal feature extraction approach shown in FIGS. 6A-6D, assisted with a neural network distortion recovery is also provided that significantly reduces the required silicon area. In some systems, a twelve-channel 55 nm CMOS test chip may be implemented. An exemplary chip shows that it consumes only 20 uW of power, which is about ten-thousand times less power than the current clinically used microprocessors. Further, the exemplary chip perform edge-computing networking operation within about 5 ms of time.

Within the application space, wearable device, e.g., cybergloves, prosthetic limbs, etc. rely on wearable high performance low power computing device to enable stringent control of assistive devices. A major bottleneck in this technology is the lack of energy efficient electronic systems that have accurate signal processing methods for sensing and classifying user intentions. To continuously improve the accuracy of motion detection, sensor fusion techniques that deploy heterogeneous sensors at any body location may be used to increase the dimensionality of biological data, which in turn produces a rich volume of information for high-fidelity classification.

FIGS. 1A and 1B illustrate an exemplary implementation of edge computing distributed neural processors of a neural network used in wearable devices 100A and 100B. In FIG. 1A, sensor fusion technique may include heterogeneous sensors such as a vision goggle 110, electromyography (EMG) sensor 112, mechanical sensor 116, motion sensors (e.g. surface electromyography sensors 132, strain sensors 138, accelerometers 134, inclinometers 136) across a human body 102 range may be fused to provide highly accurate features classification 140 on patients' motion intent 122. However, the large numbers of channels and heavy computing load created by servicing these sensors may lead to bottlenecks if channeled to a centralized processor node through a physical or wireless medium. With sensor fusion, about ten to about one-hundred channels with about eighty to about eight hundred input features need to be classified within about ten to twenty milliseconds to minimize delay and make the systems useful. As a result, heavy computation loads can pose significant challenges to modern wearable devices. Existing clinically used embedded microprocessor like the TI's OMAP4 processor, consumes six hundred milliwatts power, which can require a heavy battery to power the technology. Further, the data the processor generates may cause routing congestion and the power it consumes may discourage the use of a distributed neural network architecture because such technology distributed at or near the sensor node locations.

In FIG. 1B, the distributed neural network architecture 100B uses scalable distributed neural network processors (NP) 152, 156, 158, 160, 162 that are positioned at or near sensor node locations to perform local neural network classification. The benefits of edge computing includes a reduction in data traffic, memory consumption, and silicon use/cost. In FIG. 1B, a large neural network 100B is effectively split into distributed smaller neural networks (i.e., individual NP) with individual low dimension data 151, 153, 155, 157, 150 transferred to NP nodes for classification through the network 100B. This technology leads to significantly lower costs and reduced communication latency.

The use of edge computing in NPs reduces congestions on data movement and data computation leading to quicker response, reduced communication bandwidth requirement and reduced computing power across shorter body paths. Edge computing of the disclosed distributed neural processors enable the systems to work with local machine learning accelerators.

Figure 2:
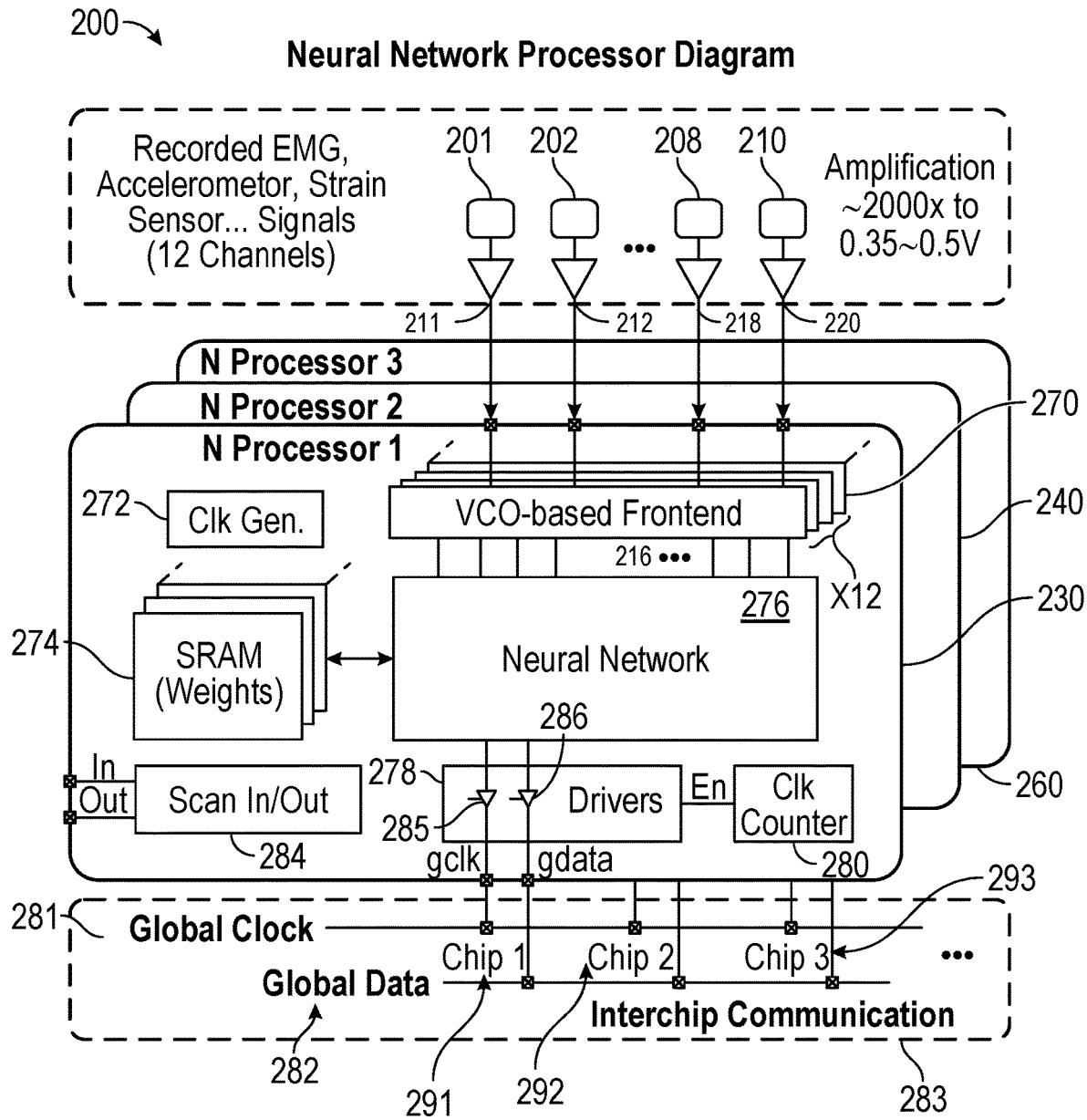
FIG. 2 is a circuit diagram of exemplary neural processors used in a distributed neural network.

FIG. 2 is a circuit diagram of exemplary neural processors 230, 240, 260 in a distributed neural network architecture 200. In FIG. 2, the neural processor 230 may include a mixed-signal processing circuit 270 (which is a VCO-based front end) at an input that directly extracts features 216 (i.e., statistical values in digital format) from analog input signals 211, 212, 218, 220 from multi-channels 201, 202, 208, 210 conveying incoming analog signals 211, 212, 218, 220 received from a sensor (e.g., an EMG sensor 132, an accelerometer 134, a strain sensor 138, etc.). The system further includes an on-chip memory banks 274 (e.g., SRAM) that stores weighted ranks that correspond with the extracted feature 216 for each sensor. Each neural processor 230 consists of two layers of neural networks, a local neural network layer 276 and a global neural network layer 283. The local neural network layer realizes dimensionality reduction for input channels clustered based on similar functionality and location. The global neural network layer 283 establishes networking and joint classification among different neural processors 240, 260.

In an exemplary application, the local neural network layer 276 includes processing circuitry 276 formed by a plurality of neuron nodes (317a-317n in FIG. 3) that process the extracted features according to their weighted ranks. The global neural network layer 283 includes processing circuitry formed by global neuron nodes (319a and b) at an output to process and classify the extracted features of the sensor and to communicate with at least one other neural processor 240 and 260 in the distributed neural network architecture 200.

While each neuron nodes (317a-317n) is only accessible by the neural processor 230 it resides in, each global neuron (319a, b) in the global layer 283 may be indexed through a global addressing scheme and may be accessed through inter-chip communications. Due to the reduction of dimensionality from local neural network layer 276, the numbers of global neurons 319a, b) are limited to be small to reduce the complexity and latency for global communication.

In an aspect of the disclosure, the on-chip memory banks 274 may store a plurality of algorithms to process the extracted features in the neuron nodes in both the local neural network layer 276 and the global neural network layer 283.

In an aspect of the system, the mixed-signal processing circuitry 270 may include an on-chip multi-channels Voltage Controlled Oscillator-based (VCO-based) frontend, where each channel of the VCO-based front end may further include at least a VCO clocked by the same on-chip clock generator 272. The system may include a plurality of comparators and counters 280 and a single-differential converter.

In FIG. 2, the global layer circuitry 283 of NP 230 may communicate processed signals as output data to neighboring NP 240 and 260 through an inter-chip communication protocol, such as through capacitive Body Channel Communication (BCC). As a result, only low dimensional data (151, 153, 155, 157 and 159 in FIG. 1B) needs to be communicated across chips 291, 292, and 293 through a single global data line 282, significantly reducing the required physical wiring connections and data traffic around a body area network. The implemented distributed neural network architecture 200 on multi-chips (291, 292, and 293) collaboratively complete features classification on large numbers of input nodes (i.e., NP 230, 240, and 270). In the local NN layer 276 design, each integrated chip of the network processor 291 may include both local and global NN layers. Only the global NN layer is communicated externally. Multiple chips 291, 292, 293 (from NP 230, 240 and 260) in the respective global layer circuitry 283 may be jointly combined to process data fusion in a larger neural network 200. The distribution of neural processors also brings the computer units closer to the sensor nodes as shown in FIG. 1B.

The distributed NP architecture provides the economic benefits of scalability as no single chip of NP needs to support a large number of sensor channels. The scalability of NP in the distributed neural network 200 provides a significant saving in silicon costs.

Figure 3:
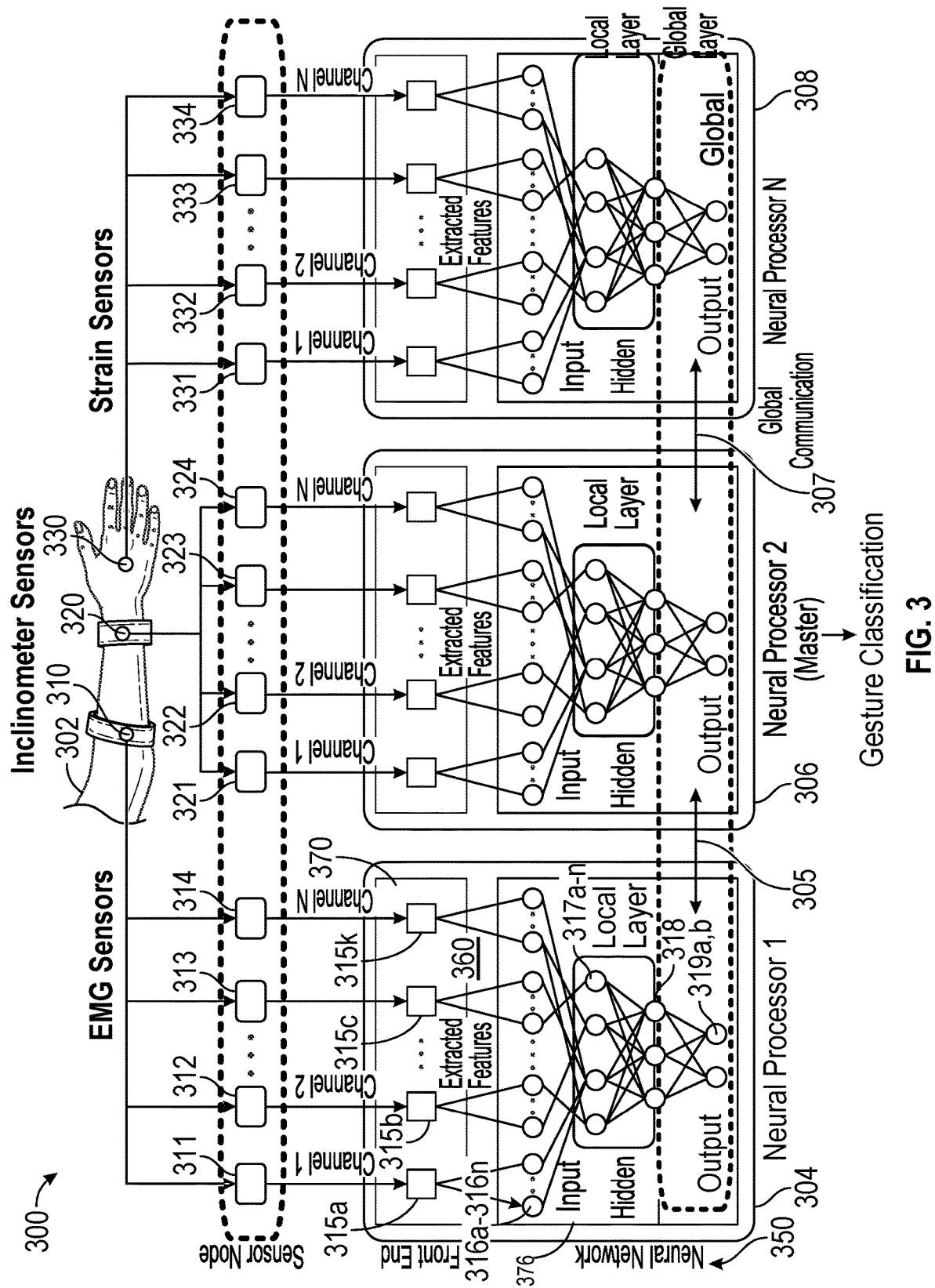
FIG. 3 is an exemplary distributed neural network that is a unitary part of a wearable device.

FIG. 3 is an exemplary distributed neural network that is a unitary part of a wearable device. In FIG. 3, incoming analog signals 311-314 are sensed raw data received from the biomedical sensors (e.g., EMG sensor 310). The data are extracted by the mixed-signal processing layer 370 (i.e., VCO-based frontend) into features 360. The features 360 are processed by a local neural network layer 376 formed by processing circuitry including an input layer of neuron nodes 316a-316n and a hidden layer of which may include a first local layer of neuron nodes 317a-317n and a second layer of neuron nodes 318.

The input layer of neuron nodes 316a-316n receive the extracted features 360 from the mixed-signal processing circuitry 370. Each of the neuron nodes 317a-317n in the first local layer is configurable to receive processed signals from one or more of the input layer of neuron nodes 316a-316n, and each of the second layer of neuron nodes 318 is configurable to receive processed signals from one or more of the neuron nodes 317a-317n in the first local layer. In some systems, the total number of neuron nodes 317a-317n in the first local layer may be fewer than the input layer of neuron nodes 316a-316n, and the second layer of neuron nodes 318 may be fewer than the total number of neuron nodes 317a-317n in the first local layer. The processed signals of the second layer of neuron nodes 318 may be routed to neuron nodes 319a,b in a global layer circuitry at the output for classification and for inter-chip global communication 305 and 307.

In FIGS. 2-3 that the global layer circuitry 283 at the output is connected to a global clock line 281 and to a global data line 282. Each global clock line 281 sends or receives a global clock signal for inter-chip communication, and the global data line 282 communicates by sending output data (i.e., computed sensor data) from the neuron nodes (317a-n, 318) of the one or both of the first and the second local layers of the neural processor 304 to another neural processor 306 or 308, or receives computed sensor data from another neural processor 306 or 308. FIG. 3 also shows that one of the NP 306 may be a master NP, which may be responsible for starting communication and providing a global clock signal 281 to synchronize the remaining neural processors 304, 308 within the distributed neural network 300.

Figure 4:
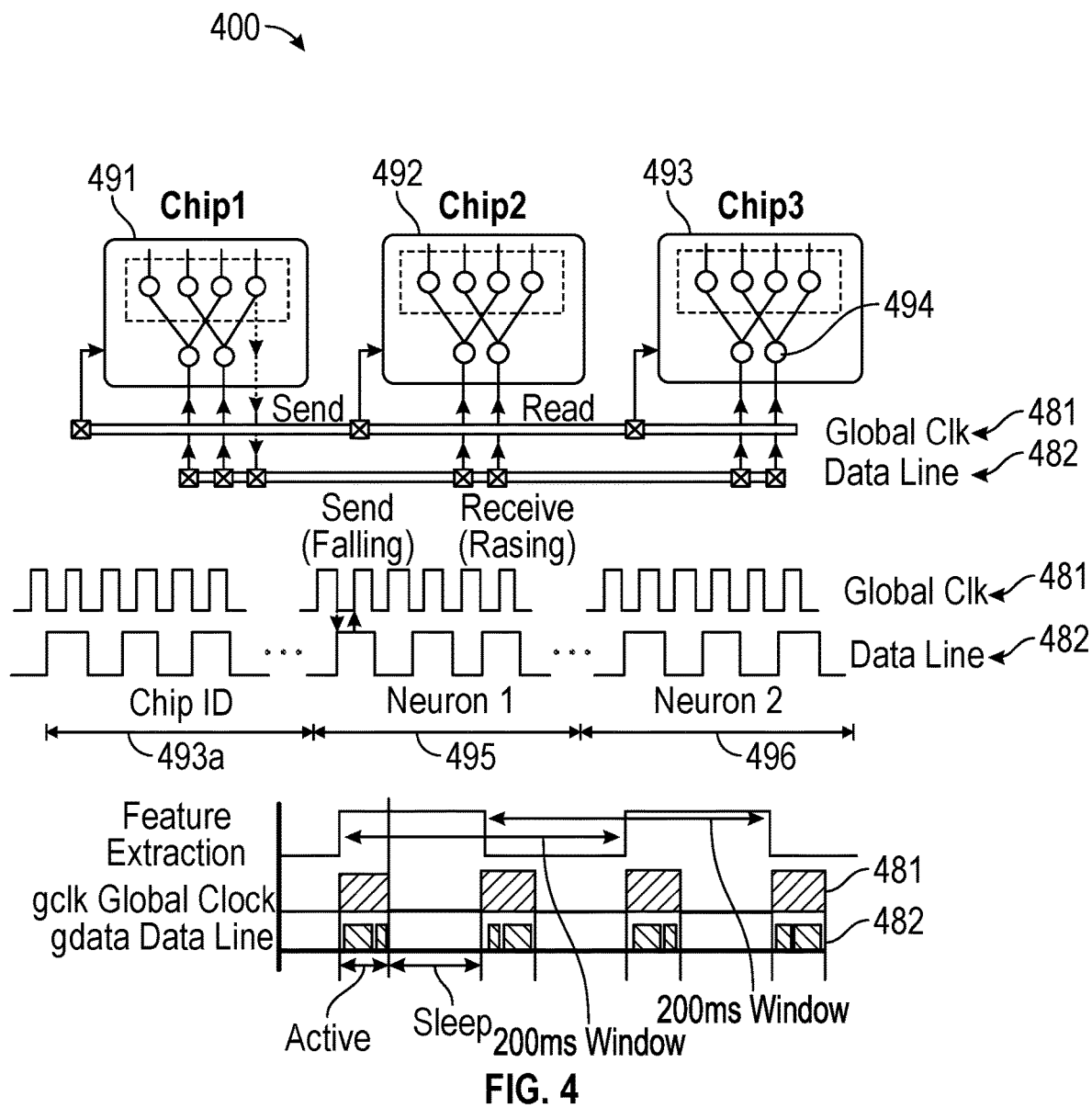
FIG. 4 is an exemplary block diagram of an inter-chip communication protocol used in a distributed neural network.

FIG. 4 is a block diagram of inter-chip communication protocol in a distributed neural network architecture 400. Chips 491, 492 and 493 may correspond to three different NPs in the respective global layer circuitry. In an example, chip 493 may be identified by a chip ID 493a which may be associated with information including how many chips, neuron nodes (e.g., neurons 495, 496) in use in the network 400. A master chip 494 (e.g., in master NP 306 in FIG. 3) may be responsible for starting communication as well as providing a global clock 481 to synchronize the remaining chips 491, 492. Each chip (e.g., chip 493) may sequentially send its hidden layer neuron output 494 to the global data bus 482. While chip 493 is sending data, all remaining chips 491, 492 in the distributed neural network 400 would be reading data from the same single-bit data line 482.

The global clock signal (gclk) 481 may synchronize individual chip clocks (such as on-chip CLK Gen 272 in FIG. 2) that may contain a slight clock frequency mismatch and may be out of phase. Master chip 493 may act as a sender chip which may send new data (gdata) to the data line 482 at a rising edge of the global clock (gclk). In some systems, this new data (gdata) may not be read by the rest of chips 491, 492 until a falling edge from the global clock (gclk) occurs. The period of the global clock, Tglobal may be several times (i.e., several magnitude) larger than the period Tlocal of the local on chip clock (such as on-chip CLK Gen 272 in FIG. 2). Since the global clock (gclk) may be several times slower than the local clock (such as on-chip CLK Gen 272 in FIG. 2), the mismatch in phase and frequency of the local clocks in different chips may not result in errors in data transmission. To keep track of what data has been sent and received, each chip 491, 492, 493 may keep counters of a current state of which bits have been sent, what neurons 495 or 496 may have been sent to and which chips (one of 491, 492, 493) may have sent data (gdata). FIG. 4 shows an exemplary communication protocol diagram for the distributed neural network architecture 400.

FIGS. 5A and 5B illustrate an exemplary optimization for distributed neural network 500A and 500B. In an example, neural network (NN) architecture 500A may be split into distributed neural processors (NP) 504, 506 to achieve edge processing. The number of distributed neural processors, e.g., parameter P may be discussed in a systematic design. Using configurable on-chip local neural network 517a-n and global neural network 518 may allow significant reduction of networking latency compared with fully connected neural network. The latency for the fully-connected MLP architecture may be expressed as equation (1).

$$t_{FC,latency} = I_t \cdot B \cdot T_{global} \quad (1)$$

in which $I_t$ represents the total number of neurons inputs, B is the number of bits for each neuron. Meanwhile the latency for the distributed NN architecture may be modeled as equation (2).

$$t_{disc,latency} = \frac{I_t}{P} \cdot T_{local} \quad (2)$$

P is the number of the distributed processors. Simulated communication latency shows an improvement with the scaling of the input neural nodes. Compared with fully connected network, in a three-chip distribution configuration, about a forty-eight to two-hundred and forty times reduction in networking latency may be observed by the distributed NN scheme.

Besides the latency, the distributed network also leads significant memory storage space reduction. The required memory 574 (e.g., on-chip SRAM) for storing the NN weights in unit of bit may be expressed by equation (3).

$$S_{MEM} = \frac{I_t \cdot N_i + \sum_{i=2}^{h} N_i \cdot N_{i-1}}{P} \cdot B \quad (3)$$

The neuron numbers within each layer may be represented by $N_i$. Simulated result may show about three to five times reduction of on-chip memory storage space 574.

While significant saving in latency, area, and power may be achieved in the networking scheme, classification accuracy may be slightly reduced compared with fully-connected network leading to a tradeoff of power and cost with accuracy. As the completion time may be important for rehabilitation applications, latency may hold a higher priority while low power may also be an important requirement for edge computing. Hence accuracy may be slightly reduced to achieve an improvement in the overall performance, e.g. reduced latency and power consumption.

The optimizations for the hidden layer number and neuron numbers of the local neural network NN may reflect the tradeoff between accuracy and area overhead may dictate the selection. For a target application, e.g., a rehabilitation with sensor fusion, the total channels (such as channels 511-530) of the input sensing signals and associated features may determine the number of input layer neurons, which may be in the order of eighty to eight-hundred input neurons in one example. Accordingly, a simulation may be performed on the choices of the hidden layers and neuron numbers. In an example, simulation results show that with more hidden layers, the NN accuracy may be improved by about one and one half percent while the space required from memory may increase by about seventy percent which lead to a two and one quarter times increase in latency as well as a three and four-tenths times increase in area. As a result, given the priority for latency and chip power, a single hidden layer may be chosen in some applications.

Also, as the number of neurons increase, the prediction accuracy does increase, the rate of increase quickly saturates from an exemplary twenty-four neuron case. Increasing the number of neurons in the hidden layer increases the communication latency since more neurons send more data. The amount of memory space needed also increases proportionally with the number of neurons added. As a result, twenty-four neurons per chip for a total of seventy-two neurons across three chips may be used in some cases to achieve a desired accuracy, memory space and latency.

Examples may be evaluated using published Ninapro database which may contain forty subjects with seventy-two channels and totaling ten hours of movement. Three types of heterogenous sensor data may be included in a database for motion detection in upper limbs (see FIG. 1A): surface EMG (sEMG) sensors 132, accelerometer sensors 134 and glove strain sensors 138. The sEMG signals may be gathered by 12 active double-differential wireless electrodes from a Delsys Trigno Wireless EMG system. The sEMG signal may be sampled at 2 kHz may then be filtered by a 50 Hz filter to reduce the noise present in body area 130. Accelerometers 134 may be used to detect the acceleration change in motion within the gesture movement. Three-axis acceleration measurement may be provided in the Delsys Trigno Wireless System, in some applications. In total, twelve accelerometer sensors with three axes per sensor may be used to generate thirty channels of acceleration data. In addition, a Cyber-Glove II may be used for strain measurement 138 at the joints of the arms. In some examples, twenty-two channels may be provided for strain measurements 138.

The use of sensor fusion techniques may create high accuracy classification on users' motion intent 140 but may also introduce a large amount of data to be processed. Different from image processing, the physiological data possesses highly stochastic biological signals. As a result, features 216 (see FIG. 2) may be extracted prior to classification. In some applications, the commonly used features of the analog signals 211-220 may be extracted including, but not limited to time-domain features of: mean, variance, the number of slope sign changes and a histogram. The number of input neurons 316-316n (see FIG. 3) for the neural network processing layer 350 may be equal to the multiplication of numbers of input channels 311-314 and features 360 used for each channel. As a result, the choices of features 360 may be important to achieve the best energy efficiency of the hardware design of the neural processor 304.

FIGS. 6A-6D illustrate exemplary mixed-signal circuitry 270 for features extraction directly from the analog signals. To reduce the overhead of the design, a mixed-signal feature extraction design may be described which directly convert the analog signals into features of statistical values in digital format for the neural network classification. Conventional design uses high precision analog-digital converter (ADC) to process received analog sensor signal to the digital domain. In addition, a digital block for digital feature extractions (DFE) may be required to convert the digital signal back into time-domain features, e.g. mean, variance, histogram, slope sign change, etc. The mixed-signal processing circuitry 270 may remove this conventional two-step process by combining the front-end ADC and DFE into a simple direct mixed-signal feature extraction unit leading to a twenty-eight times saving in time.

The mixed signal processing circuitry 270 may include a feature extraction unit which calculates statistical values and various time-domain features, e.g., a mean, a variance, a slope-sign change, and five histogram bins. The mixed-signal processing circuitry 270 in FIGS. 6A-6D may execute a direct analog signals extraction of statistical values into a digital format using only a voltage-controlled oscillators (VCOs) based front end, comparator and counters, etc.

Figure 6A:
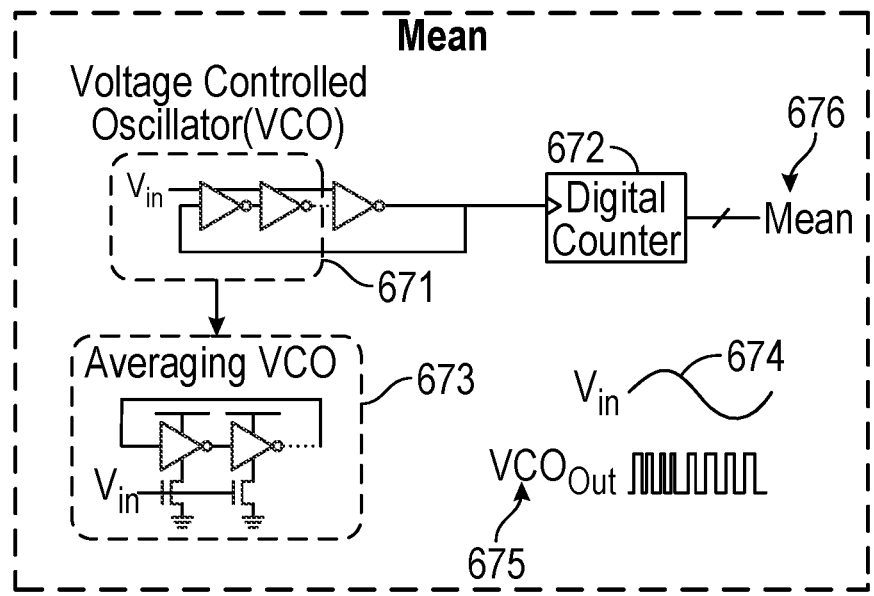
FIGS. 6A through 6D are exemplary mixed-signal circuitry that extract features.

In FIG. 6A, analog signals from sensors may have an incoming signal Vin 674 bandwidth of a few kHz. VCOs 671 may run at sub-threshold region between 10-300 kHz speed and deliver pulses VCO out 675 to subsequent counters 672 for feature extraction. To calculate a mean feature 676, VCO's output 675 may be transmitted to a counter 672. Since the mean 676 is proportional to a sum of all the events, this may be used as the mean feature eliminating the need for an expensive digital calculation on the mean feature and analog-to digital conversion. An ideal mean calculation may be represented by equation (4). The VCO based mean calculation may be expressed by equation (5).

$$Mean_{ideal} = \sum_{i=1}^{N} \frac{Vin(i)}{N} \quad (4)$$

$$Mean_{vco} = \int_{0}^{N} VCO(Vin(i)) \quad (5)$$

N represents a total number of examples in a window and Vin represents the voltage. The VCO function may convert a voltage at time i into a count value that may be accumulated.

Figure 6B:
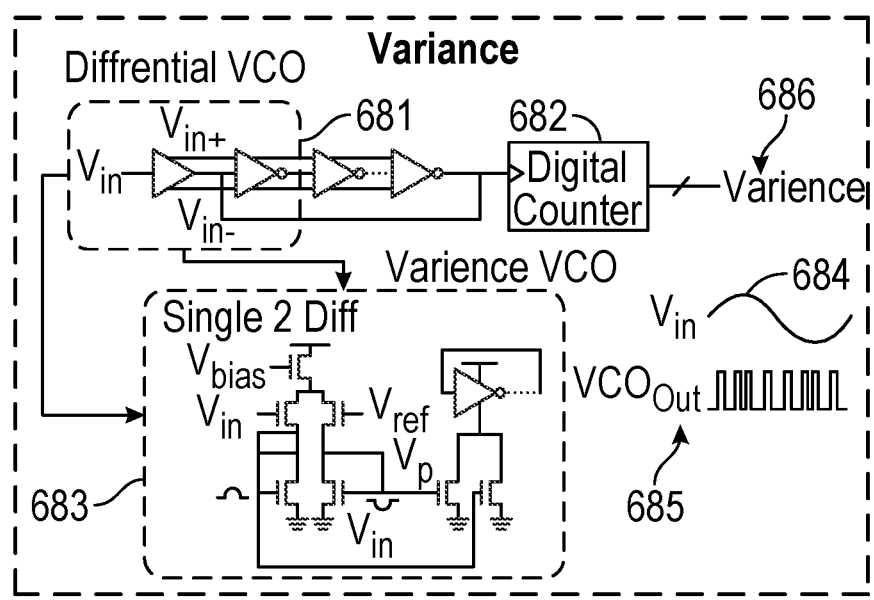

In FIG. 6B, an ideal variance calculation may be represented by equation (6). The VCO based variance may be expressed by equation (7).

$$Var_{ideal} = \sum_{i=1}^{N} \frac{(Vin(i) - \mu)^2}{N} \quad (6)$$

$$Var_{vco} = \int_{0}^{N} VCO(Vin(i) - \mu) \quad (7)$$

in which μ is the average value of this channel. Like the mean VCO function, the variance VCO function 681 may convert the voltage at time i into a count value that may be accumulated. The overall design structure may be similar to the mean. The VCO however is modified to take in a differential signal (i.e., Vin and Vref). The incoming analog signal Vin may be sent through a differential amplifier 683 to modulate VCO speed according to signal's deviation from its average input. A distance may be calculated from an average value to approximate an ideal variance operation.

Figure 6C:
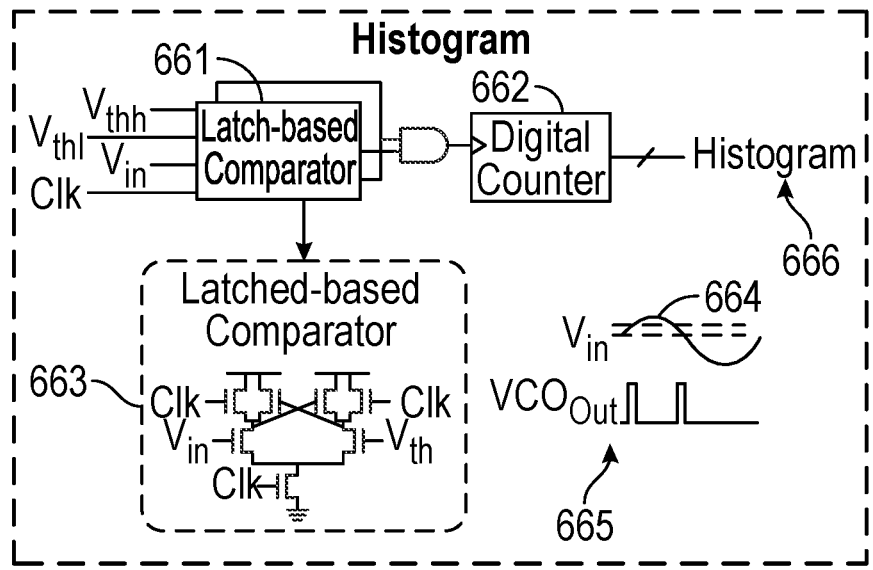
Figure 6D:
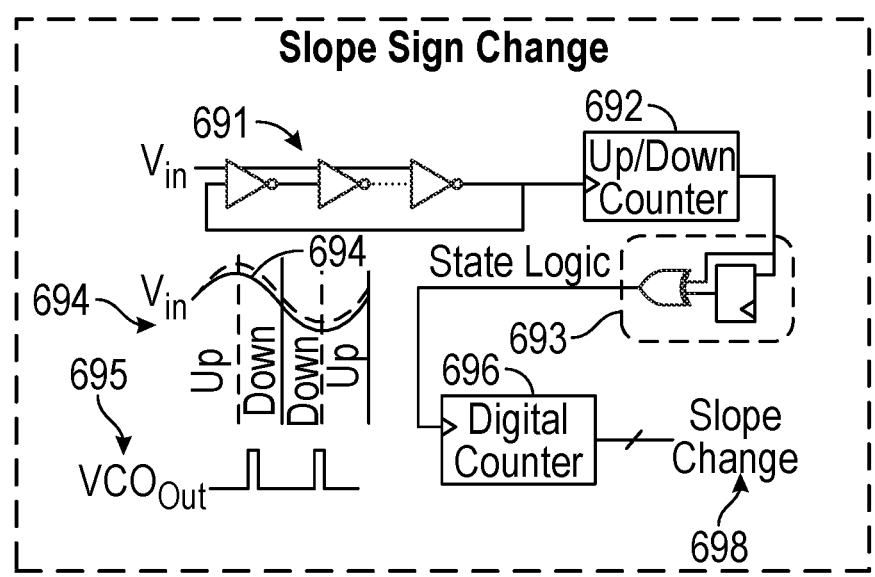

In FIG. 6D, a calculation for a slope sign change may be represented by equation (8).

$$SSC = \sum \left[ \text{sign}\left(\frac{dVin(i)}{dt}\right) \neq \text{sign}\left(\frac{dVin(i-1)}{dt}\right) \right] \quad (8)$$

The slope sign change feature may use a bi-directional counter 692 with the mean VCO 691. For one millisecond, this counter 692 will count up followed by one millisecond where the counter 692 will count down. The most significant bit (MSB) of the counter 692 may yield a result which is then compared with that from a previous 2-millisecond cycle. If this bit (MSB) has changed, it may be determined that the slope sign has changed and may increment an output counts.

In FIG. 6C, a calculation for histogram may be shown in equation (9).

$$Hist = \sum_{bin\ n}^{B} \sum (Vin(i) > Vth(n)_l\ \&\ Vin(i) < Vth(n)_h) \tag{9}$$

where B is the total number of bins, $Vth(n)_l$ may be a lower bound of bin n and $Vth(n)_h$ may be a lower bound of bin n. To calculate the histogram 666 of the inputs, the channel voltage may be sent to a series of clocked comparator 663 with various levels of reference voltages 664 to determine what bin range the voltage fell into. The clocked comparators 663 may be triggered once every millisecond and produce a clock like pulse 665 which may be sent to a counter 662. Each bin range may have a separate counter.

Despite of dramatic saving from a scheme by removal of ADC, such a VCO based conversion method may lead to strong distortion in the feature obtained. Non-linear relationship between input voltage and count generated. At the top end of the distribution, the count shows a decrease in linearity while the bottom end also loses some of the linearity as well. For the mean feature, this distorted curve may be modelled as equation 10.

$$Mean = -1.5x^4 + 0.5x^3 + 2.3x^2 - 0.1x \tag{10}$$

x represents the normalized signal value coming from a sensor.

The features mean and variance may show distortion from VCOs because the speed of the VCO may not be linear with respect to the voltage input Vin due to the operation in the near/subthreshold region of the transistors in VCO. There may be a loss of functional mapping between the ideal floating-point feature value and the VCO circuit implementation-based design.

As seen in equation (10), the near-threshold operation of VCO may produce a strong 2nd and 4th order distortion leading to a collapse of feature spaces and degradation from linear classifiers. Such a distortion may lead to significant degradation from commonly used classifier, e.g. simple linear SVM. However, the degradation from neural network (NN) processing circuitry 270 is only one percent thanks to a strong nonlinear operation of neural network processing circuitry 276. The training of NN processing circuitry 270 using the distorted feature characteristics may lead to a recovery of the accuracy loss from the low-cost feature extraction circuits.

Given that the feature data is of a similar magnitude data will tend to have much smaller weights after training. This reduces the focus of the results on the distorted data and in turn moves it to less distorted features. This occurs within some individual weights associated with features as well as entire neurons if the results fed to the neuron are quite distorted. The error for each weight may be calculated using equation (11).

$$Error = (L_2 Norm(\sigma(O_W \cdot \sigma(H_W \cdot I))) - t) \tag{11}$$

in which OW represents output weights, HW represents hidden weights, and σ represents the activation function. I is the input vector and t the target vector for the example in question. The change in weights are calculated by equation (12).

$$\Delta O_W = (d\sigma(O_W \cdot H_V))(O_V - t) \tag{12}$$

OV represents an output of the output layer and HV represents the output of the hidden layer. If the data is distorted, the delta weight values would remain large over time. Features that contain inconsistent results within the neural network would have a much tougher time creating a consistent impact on the for the backpropagation weights causing these values to go back and forth. The neural network will filter out these inconsistent features through the backpropagation algorithm. Overall, the use of neural network allows elimination of expensive analog front-end, e.g. ADC, leading to significant saving of silicon area. The mixed-signal architecture highlights another contribution from machine learning technique to modern electronic design.

FIGS. 7A and 7B illustrate exemplary neural processor reconfiguration to implement on-chip machine learning. FIG. 7A shows an exemplary proposed topology design of a neural network processing layer 350A may be configured into a neural network processing layer 350B with many different architectures, e.g., conventional neural networks, recurrent neural networks, multi-layered perceptrons, Restricted Boltzmann Machines, etc. Neurons (316a-n, 317a-n, 318a-d) at both local network layer and neurons (319a-b) at global layer circuitry) inside the processors (304, 306, 308) may individually be regrouped, reconfigured and reconnected through crossbar connections into different topologies. Different commonly used activation functions such as Sigmoid, ReLU, Softmax may be supported. Gibbs sampling, random number generators and logarithmic operations that are required by topologies such as Hidden Markov Models or RBM may also be available. The assignment of neurons (316a-n, 317a-n, 318a-d, 319a-b) into each layers of network is fully configurable to achieve the best tradeoff and optimization for each special application.

In addition, the processing may accommodate complex feature extractions 380, e.g. Fast Fourier Transforms, Discrete Wavelet Transforms, which may sometimes be used in special applications such as cardiac or audio signal processing which typically require significant hardware resources. Benefits from an availability of large numbers of neurons which may contain basic arithmetic units such as multipliers, adders may provide capability to reconfigure the numbers of neurons into the specific mathematic operations that may be required by FFT and DWT. Hence, without creating dedicated processing units, neurons may be reused to maximize a usability of the neural processor 304 to overcome its limitation on supported functions.

FIG. 7B also show a high-level view of an implementation of on-chip machine learning in a proposed neural processor design. Strong re-configurability may be built for neural nodes NE of a local layer and a global layer of a neural processor 304. Crossbars 383, 385, 387 may interconnect with SRAM banks 274a-274p to allow configuration of neuron nodes NE of the local layer of neural network processing circuitry into different structures, e.g. recurrent neural network. Bi-directional signal propagations in the neuron nodes NE (316a-n, 317a-n, 318a-d) of the local layer of neural network processing circuitry into different neural network structures, e.g. recurrent neural network (RNN). Bi-directional signal propagations in the neuron nodes NE (319a, b) of the global layer may be reconfigured for supporting Gibbs sampling and learning operation. Neurons nodes FE in front layers may be also reconfigured into special arithmetic units for complex feature extractions.

Other examples of on-chip training reconfigurations may include reconfiguring the neuron nodes NE (316a-n, 317a-n, and 318a-d) in the local neural network layer (e.g., 276 in FIG. 2) and the neuron nodes (319a, b) in global network layer (e.g., 283 in FIG. 2) to: enable or disable certain neuron nodes NE in the local layer, increase or decrease bit widths of weights, reallocate memory assignment in the memory banks (i.e., SRAM 274a-274p), reconfigure neuron nodes NE functionality and feature extension, modify feature configuration, activation function, learning mechanism, networking configuration and active power and clock gating in the neuron processor.

FIGS. 8A and 8B illustrate exemplary capacitive body channel communication (BCC) among neural processors 852, 856, 858 in a distributed body neural network 800. It is shown that Body channel communication may utilize human body 850 as a communication media for signal propagation 851, 853. Human body 850 may exhibit sufficiently high conductivity for capacitive coupling BCC. The BCC approach may subject to stringent regulation on current level leading to slow data rate at only kb/s rate.

On the other hand, capacitive coupling BCC does not inject any electrical current into body. Instead, it relies on the capacitive coupling through air and earth to establish communication among devices such as neural processors 852, 856, 858, and hence does not incur significant concern of medical safety and regulation. As a result, much higher communication rate may be supported. Nevertheless, capacitive BCC suffers from higher loss than Galvanic coupling. BCC and has to deal with a variant connectivity due to the nature of floating ground in its transmitter and receiver. As a result, more design challenges are presented to capacitive BCC communication. This proposal will be focused on developing low cost networking solution using capacitive BCC due to its support of high data rate and less concern on medical regulation.

Several significant progresses have been made recently in building Capacitive BCC devices. A capacitive BCC transceiver (includes transmitter 810) may demonstrate with up to a data transmission rate of 150 Mb/s using customized IC chip. The transceiver consumed 1~2 mW power with extremely tiny silicon area of 0.1 mm$^2$. The design may be very similar to a serializer/de-serializer (SerDes) used in conventional wireline communication for communication between CPU and Memory. If a human body is modeled as an integrated computing system, the use of BCC may provide an ideal solution for the device-to-device communication due to its low cost, high data rate and relatively concealed environment, similar to a printed circuit board used in modern electronic system. Compared with an existing WIFI communication, transceiver power silicon cost may be reduced while data rate may be kept similar or above. In addition, the neural processor device 852 may be made much smaller owing to the elimination of antenna which may dominate the size of the system.

To facilitate the design of BCC based networking device for our "whole-body" computing scheme, a balun transformer may be used to provide an isolation of the ground in the communication simulating the real device-to-device communication without common ground. FIG. 8B shows a proposed simple low-cost transceiver design for use in our distributed neural processor. The design may be further simplified by eliminating a front-end equalizer and the requirement to synchronize the clocks. Instead, a simple error correction circuit may be used to eliminate the noise or glitches due to unmatched channel profiles. The simulation waveform on the proposed circuit shows that a data stream 811 may be transmitted at a frequency of 80 MHz despite of the noisy channel response due to the mismatch of the channel impedance.

FIG. 9 depicts a feature rank score chart for individual heterogeneous sensor when optimized for fusing data or combining features from different sensors. Different sensors or heterogeneous sensor such as EMG 132, accelerometers 136 may contain different signal characteristics (i.e., features). It may be important in some systems to develop a methodology to analyze the significance of each feature for each sensor channel 311-314. A statistical evaluation method may rank the features according to its contribution to the final accuracy. To achieve, a two-sample Kolmogorov-Smirnov statistical test may be used, where a distribution of data points to another distribution of data points belonging to another label may be compared in order to create a matrix of comparison of how different the data from each label is from each other.

This procedure is given in an example Algorithm 1 below:

```
Algorithm 1 Feature Rank
Procedure Feature Rank (sensors, label_list, channel_list, feature_list, data)
foreach k ∈ sensors do
    //finding the similarity for each feature
    foreach feature ∈ feature_list do
        foreach channel ∈ channel_list do
            data_s←get_feature(data, channel, feature, sensor)
            foreach i ∈ label_list do
                foreach j ∈ label_list && j > i do
                    dist1←extract_distribution(data_s, i)
                    dist2←extract_distribution(data_s, j)
                    score_m(i,j)←two_sample_ttest (dist1, dist2)
                end for
            end for
            channel_s(channel)←mean(score_m)
        end for
        feature_scores(sensor,feaure)←mean (channel_s)
    end for
end for
return sort(feature_scores) //return the order of all the scores
```

The above algorithm data may represent the full dataset used. Sensors is a list of the types of sensors such as EMG 132, accelerometers 134 and strain glove 125. The label_list is a list of all possible labels. Channel_list is the channels associated with each sensor. Feature_list is a list of the types of features being analyzed. The above algorithm code may loop through every feature for every channel for every sensor and calculate a ranking score or a weighted rank for that channel. To do this, data (analog signals 211-220 in FIG. 2) from a feature for a channel 201-210 may be divided into sections. These sections may be grouped with examples with matching labels.

To calculate a ranking score or weighted rank, a two-sample test may be run on each of the distributions to determine how different labels may affect the distribution. Every combination may be averaged together to create one score for this channel's feature. Features of channels that shows low differentiation among different labels would provide data that is more ambiguous than features of that with high scores leading to confusion and difficulty for classification. Such a result may vary from channel (e.g., 201) to channel (anyone of 202-210). Once this is done for all channels feature combinations, scores (see FIG. 9) may be aggregated by sensor type (sEMG, accelerometer, inclinometer, strain sensor, etc.,) and feature type to create a score (e.g., any value between 0 and 1) for each combination of feature and sensor.

FIG. 9 shows normalized scores given to features based on the feature rank method. For the sEMG channels, variance is the important signal. For accelerometers, the mean feature may be more important than the variance as well as some of the higher range histogram bins. The strain sensors from cyberglove values all the features although the mean, variance is more significant.

In an example, feature space reduction may be implemented by removing various features to reduce weight required by the neural network processing circuitry 276 as well as power saving from feature extraction. Choosing the right features for certain sensors may minimize an impact on accuracy. Search space optimization may be implemented by removing as many features from various sensors as possible while maintaining an accuracy loss within one percent. Using the feature ranking method in Algorithm 1, the search space of the optimization problem may be simplified. Simulations may show that a neural network processing circuitry 276 may be divided into three sections with different sensors for each section. Algorithm 2 shows the pseudo codes for feature selection.

Algorithm 2 Optimizing Features Selection

---

Procedure neural_network_prunning (ranked_feature, max_accuracy)
performance←mac_accuracy
while max_accuracy-performance < one percent do
    HiddenWeights←remove_feature(rank_feature(i))
        performance←nn_classification (HiddenWeights)
        i←i+1
    end while
return i−1 //return how many features were removed.

---

The ranked_feature is a list of ranked features determined by the rank feature procedure described in Algorithm 1. The max_accuracy is an accuracy attained without removing any features. The algorithm loops through the list of the worst ranked features and removes the links to that feature within the hidden weights. After this is done, training and testing procedure of the neural network may be run without that removed feature to obtain a prediction accuracy. The procedure may be repeated to a next lowest feature until significant performance loss, e.g., one percent is observed. It may be shown that there are twenty-four feature combinations in total. The ranked feature algorithm allows eight different feature combinations to be removed while keeping the accuracy reduction within one percent. If four features are chosen at random, the accuracy loss may exceed one percent. Tolerating a loss of one percent may reduce the amount of memory required by an additional twenty-percent when using the feature ranking method with a result of a reduction of computing power.

In an implementation, weighted rank may be stored in memory banks 274 (SRAM) and the weighted rank may correspond to a number of bits for each neuron. In on-chip machine learning, the weighted rank for the sensor may be updated for reclassifying the extracted features of the sensor. In another implementation, a bit number between eight to ten may be assigned to the total neuron nodes in the hidden layer to reduce power consumption in the neural processor. In another implementation, an eight-bit on-chip learning may be enabled by a stochastic rounding process implemented through an on-chip random number generators using linear feedback shift register (LFSR). The eight-bit on-chip learning may be enabled by pre-loading globally trained weights, where accuracy may be improved through sequentially sending batch training data into the neuron nodes in the hidden layer, and a random number generator based on linear feedback shift register (LFSR) which is used to randomize training sequence for each batch during the on-chip learning.

Although various aspects of the claimed subject matter have been described herein, such aspects need not be utilized in combination. It is therefore intended that the appended claims cover all such changes and modifications that are within the scope of the claimed subject matter.

I claim:

1. A neural processor for edge computing in a distributed neural network, comprising an integrated chip that comprises:
    mixed-signal processing circuitry at an input that extracts features from multi-channels of incoming analog signals received from a sensor, wherein the features that are extracted comprise statistical values in a digital format from the incoming analog signals;
    on-chip memory banks that store weighted ranks to correspond to the features that are extracted for the sensor;
    a local neural network layer formed by processing circuitry comprising a plurality of neuron nodes that process the features that are extracted based on their weighted ranks; and
    a global network layer formed by the processing circuitry comprising global neuron nodes at an output that process and classify the features that are extracted of the sensor and communicate with at least one other neural processor within the distributed neural network,
    wherein the mixed-signal processing circuitry comprises an on-chip multi-channels voltage controlled oscillator-based front end,
    wherein each channel of the voltage controlled oscillator-based front end further includes at least a voltage controlled oscillator clocked by a same on-chip clock generator, a plurality of comparators and counters and a single-differential converter.

2. The neural processor according to claim 1, wherein the mixed-signal processing circuitry is devoid of an analog to digital converter in the neural processor, wherein the mixed-signal processing circuitry extracts the features from the incoming analog signals as time-domain features of: a mean, a variance, a slope absolute value, a histograms and a zero crossings.

3. The neural processor according to claim 2, wherein the mean is generated by the voltage-controlled oscillator and an output of a counter which calculates averages counts of the voltage-controlled oscillator within an overlapped time window.

4. The neural processor according to claim 2, wherein the variance is generated by the voltage-controlled oscillator and another reference voltage-controlled oscillator in conjunction with a bidirectional counter that accumulate a distance from the mean over a time window.

5. The neural processor according to claim 2, wherein the slope absolute value is generated by a bidirectional counter which compares a difference in voltage between two-timing windows.

6. The neural processor according to claim 1, wherein the local neural network layer comprises an input layer having It neuron nodes and a hidden layer having at least a first local layer of Ni neuron nodes, wherein the input layer having It neuron nodes receives the features that are extracted from the mixed-signal processing circuitry, and each of the Ni neuron nodes is configurable to receive processed signals from one or more of It neuron nodes, wherein Ni<It.

7. The neural processor according to claim 6, wherein the hidden layer comprises a second local layer of Nk neuron nodes, wherein each of the Nk neuron nodes is configurable to receive processed signals from one or more of the Ni neuron nodes, wherein Nk<Ni.

8. The neural processor according to claim 7, wherein the global network layer at the output is connected to a global clock line and to a global data line, wherein the global clock line sends or receives a global clock signal used for interchip communication, and the global data line is configured to communicate by sending computed sensor data from the neuron nodes of the one or both of the first and the second local layers of the neural processor to another neural processor, or receive computed sensor data from another neural processor.

9. The neural processor according to claim 1, wherein the weighted ranks correspond to a number of bits for each neuron.

10. The neural processor according to claim 9, wherein the weighted rank for the sensor is updated in machine learning for reclassifying the features that are extracted of the sensor.

11. The neural processor according to claim 9, wherein the neural processor is programmed to execute a stochastic rounding process or stochastic batching processing techniques to improve a precision due to a reduction in a plurality of bit numbers to total neuron nodes in a hidden layer.

12. The neural processor according to claim 9, wherein an eight-bit on-chip learning is enabled by a stochastic rounding process implemented through an on-chip random number generator using linear feedback shift register.

13. The neural processor according to claim 9, wherein an eight-bit on-chip learning is enabled by pre-loading globally trained weights, where accuracy is improved through sequentially sending batch training data into the neuron nodes in a hidden layer, and a random number generator based on linear feedback shift register is used to randomize training sequence for each batch during the on-chip learning.

14. The neural processor according to claim 13, wherein the on-chip memory banks are overwritten by the pre-loaded globally trained weights during on-chip learning.

15. The neural processor according to claim 9, wherein the on-chip memory banks are crossbar connected with the plurality of neuron nodes in a hidden layer and global processing layer to form recurrent neural network to allow bidirectional signal propagations to support learning operations.

16. A neural processor for edge computing in a distributed neural network, comprising an integrated chip that comprises:
mixed-signal processing circuitry at an input that extracts features from multi-channels of incoming analog signals received from a sensor, wherein the features that are extracted comprise statistical values in a digital format from the incoming analog signals;
on-chip memory banks that store weighted ranks to correspond to the features that are extracted for the sensor;
a local neural network layer formed by processing circuitry comprising a plurality of neuron nodes that process the features that are extracted based on their weighted ranks; and
a global network layer formed by the processing circuitry comprising global neuron nodes at an output that process and classify the features that are extracted of the sensor and communicate with at least one other neural processor within the distributed neural network,
wherein a distributed neural network architecture is formed by a plurality of neural processors that each extracts and processes features from a respective sensor local to a respective neural processor, wherein one of the plurality of the neural processors comprising a master neural processor which is responsible for starting communication and providing a global clock signal to synchronize remaining neural processors within the distributed neural network.

17. The neural processor according to claim 16, wherein one of the neural processors in the distributed neural network architecture sequentially sends its hidden layer neuron data output to a global data line and all remaining neural processors in the distributed neural network architecture read the data output from the one neural processor from the global data line.

18. A neural processor for edge computing in a distributed neural network, comprising an integrated chip that comprises:
mixed-signal processing circuitry at an input that extracts features from multi-channels of incoming analog signals received from a sensor, wherein the features that are extracted comprise statistical values in a digital format from the incoming analog signals;
on-chip memory banks that store weighted ranks to correspond to the features that are extracted for the sensor;
a local neural network layer formed by processing circuitry comprising a plurality of neuron nodes that process the features that are extracted based on their weighted ranks; and
a global network layer formed by the processing circuitry comprising global neuron nodes at an output that process and classify the features that are extracted of the sensor and communicate with at least one other neural processor within the distributed neural network,
wherein the local neural network layer comprises an input layer having It neuron nodes and a hidden layer having at least a first local layer of Ni neuron nodes, wherein the input layer having It neuron nodes receives the features that are extracted from the mixed-signal processing circuitry, and each of the Ni neuron nodes is configurable to receive processed signals from one or more of It neuron nodes, wherein Ni<It,
wherein the hidden layer comprises a second local layer of Nk neuron nodes, wherein each of the Nk neuron nodes is configurable to receive processed signals from one or more of the Ni neuron nodes, wherein Nk<Ni,
wherein the neuron nodes at the hidden layer are configurable for regrouping and reconnecting through crossbar connections into different topologies to achieve trade off and optimization during on-chip learning.

19. A method of processing signals from a biomedical device, comprising:
attaching a biomedical device to a human body part, wherein the biomedical device comprises a neural processor coupled to at least one sensor which sends multi-channel analog signals of detected physiological activities to the neural processor, and wherein the biomedical device is one of a plurality of biomedical devices that form a distributed neural network;
directly extracting, by mixed-signal processing circuitry of the neural processor, features from multi-channel analog signals received from the at least one sensor, wherein the features that are extracted are statistical values in a digital format from analog signals, wherein the mixed-signal processing circuitry consists of an on-chip multi-channels voltage controlled oscillator-based frontend, wherein each channel of the voltage controlled oscillator-based front end further includes at least a voltage controlled oscillator clocked by a same on-chip clock generator, a plurality of comparators and counters and a single-differential converter;

executing program code stored in on-chip memory banks to configure the neural processor to process the features that are extracted, wherein the features that are extracted are processed according to weighted ranks corresponding to the features that are extracted and the weighted ranks are locally stored in the on-chip memory banks;

the processing of the features that are extracted comprising processing by a local neural network layer and a global network layer of the neural processor, wherein the local neural network layer is formed by processing circuitry comprising a plurality of neuron nodes that process the features that are extracted according to their weighted ranks, and the global network layer is formed by processing circuitry comprising global neuron nodes at an output to process and classify the features that are extracted of the at least one sensor; and communicating through a global data line of the neural processor, the features that are extracted and classified with at least one other biomedical device within the distributed neural network.

* * * * *